(12) United States Patent
Erdmann et al.

(10) Patent No.: US 9,943,221 B2
(45) Date of Patent: Apr. 17, 2018

(54) MEDICAL, IN PARTICULAR DENTAL, DIAGNOSTIC DEVICE HAVING IMAGE CAPTURE MEANS

(75) Inventors: Sven Erdmann, Ulm (DE); Andre Hackel, Mittelbiberach (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 552 days.

(21) Appl. No.: 13/256,054

(22) PCT Filed: Mar. 17, 2010

(86) PCT No.: PCT/EP2010/053464
§ 371 (c)(1),
(2), (4) Date: Oct. 21, 2011

(87) PCT Pub. No.: WO2010/106102
PCT Pub. Date: Sep. 23, 2010

(65) Prior Publication Data
US 2012/0034573 A1  Feb. 9, 2012

(30) Foreign Application Priority Data
Mar. 17, 2009 (DE) .................. 10 2009 013 615

(51) Int. Cl.
*A61B 1/00* (2006.01)
*A61B 1/253* (2006.01)
(Continued)

(52) U.S. Cl.
CPC ............ *A61B 1/253* (2013.01); *A61B 1/0008* (2013.01); *A61B 5/0059* (2013.01);
(Continued)

(58) Field of Classification Search
CPC ....... A61B 1/127; A61B 1/05; A61B 1/00096; A61B 1/0008; A61B 1/253; A61B 5/0088; A61B 5/0059; H04N 1/00986
USPC .............. 600/169, 109, 160, 129, 110, 157; 433/29, 30, 27, 31; 606/27; 348/65, 66; 359/512, 820; 219/522
See application file for complete search history.

(56) References Cited

U.S. PATENT DOCUMENTS 709,812 A * 9/1902 Bennett et al. ................ 219/219
1,934,110 A * 11/1933 Wilson .......................... 219/219
(Continued)

FOREIGN PATENT DOCUMENTS

DE   102008031881 B3   6/2009
JP   10-511298          11/1998
(Continued)

OTHER PUBLICATIONS

International Search Report for PCT/EP2010/053464 dated May 20, 2010.
(Continued)

*Primary Examiner* — Timothy J Neal
*Assistant Examiner* — Aaron B Fairchild
(74) *Attorney, Agent, or Firm* — Marshall, Gerstein & Borun LLP (57) ABSTRACT

A medical, in particular dental, diagnostic device having means for image capture and a hand piece that has a window located in the optical path of the means for image capture, wherein there are means for heating the window formed by a resistance heater.

13 Claims, 5 Drawing Sheets

(51) Int. Cl.
*A61B 5/00* (2006.01)
*A61B 1/05* (2006.01)
*A61B 1/12* (2006.01)

(52) U.S. Cl.
CPC .............. *A61B 5/0088* (2013.01); *A61B 1/05* (2013.01); *A61B 1/127* (2013.01)

(56) References Cited

U.S. PATENT DOCUMENTS

| | | | |
|---|---|---|---|
| 3,495,259 A * | 2/1970 | Hertel et al. ................ | 219/522 |
| 4,076,018 A * | 2/1978 | Heckele ....................... | 600/168 |
| 4,279,246 A * | 7/1981 | Chikama ...................... | 600/169 |
| 4,468,197 A * | 8/1984 | Provost ........................ | 433/30 |
| 4,568,281 A | 2/1986 | Harvey et al. | |
| 4,722,000 A * | 1/1988 | Chatenever ........ | A61B 1/00195 600/169 |
| 5,016,098 A * | 5/1991 | Cooper et al. ................ | 348/66 |
| 5,536,236 A * | 7/1996 | Yabe et al. ................... | 600/125 |
| 5,605,532 A * | 2/1997 | Schermerhorn ............ | 600/169 |
| 5,818,587 A * | 10/1998 | Devaraj et al. .............. | 356/477 |
| 5,986,693 A | 11/1999 | Adair et al. | |
| 6,503,196 B1 * | 1/2003 | Kehr et al. ................... | 600/176 |
| 6,712,479 B1 * | 3/2004 | Seitzinger et al. ........... | 359/512 |
| 6,866,391 B2 * | 3/2005 | Krausse ....................... | 359/512 |
| 7,455,637 B2 * | 11/2008 | Takahashi .................... | 600/169 |
| 7,938,774 B2 * | 5/2011 | Segawa ........................ | 600/169 |
| 8,029,438 B2 * | 10/2011 | Hagihara et al. ............ | 600/169 |
| 8,142,351 B2 * | 3/2012 | Aono et al. .................. | 600/167 |
| 8,172,409 B2 * | 5/2012 | Nagamizu .................... | 359/512 |
| 8,206,288 B2 * | 6/2012 | Wieters et al. .............. | 600/169 |
| 8,462,202 B2 * | 6/2013 | Takahashi .................... | 348/76 |
| 8,485,967 B2 * | 7/2013 | Takahashi et al. .......... | 600/169 |
| 8,556,625 B2 * | 10/2013 | Lovely ......................... | 433/29 |
| 8,602,978 B2 * | 12/2013 | Segawa ........................ | 600/169 |
| 2005/0024646 A1 * | 2/2005 | Quadling et al. ............ | 356/477 |
| 2007/0073108 A1 * | 3/2007 | Takahashi .................... | 600/169 |
| 2007/0134615 A1 * | 6/2007 | Lovely ......................... | 433/29 |
| 2007/0149856 A1 * | 6/2007 | Segawa ........................ | 600/169 |
| 2008/0108012 A1 * | 5/2008 | MacArthur ................... | 433/31 |
| 2008/0228035 A1 * | 9/2008 | Hagihara et al. ............ | 600/121 |
| 2008/0231695 A1 * | 9/2008 | Favonio ....................... | 348/65 |
| 2008/0239071 A1 * | 10/2008 | Takahashi .................... | 348/76 |
| 2009/0177038 A1 * | 7/2009 | Yashiro et al. .............. | 600/132 |
| 2010/0010313 A1 | 1/2010 | Muckner et al. | |

FOREIGN PATENT DOCUMENTS

| | | |
|---|---|---|
| JP | 2004-188211 A | 7/2004 |
| WO | WO-9731293 A1 | 8/1997 |

OTHER PUBLICATIONS

Office Action for Japanese Application No. 2012-500239, dated Jan. 22, 2014.

* cited by examiner

MEDICAL, IN PARTICULAR DENTAL, DIAGNOSTIC DEVICE HAVING IMAGE CAPTURE MEANS

BACKGROUND OF THE INVENTION

Field of the Invention

The present invention relates to a medical, in particular dental, diagnostic device, which has means for image capture and has a handpiece with a window situated in the beam path of the means for image capture, with provision furthermore being made for heating the window. In particular, the present invention relates to a so-called intraoral camera or a system for transilluminating teeth.

Related Technology

In medicine, in particular dentistry, use is increasingly made of diagnostic systems that are based on optical principles. The reason for this is that such devices usually allow a diagnosis to be made without contact, i.e. in particular without pain, and moreover generally also provide optical images that can be used to impart a better understanding about possibly required therapeutic measures to the patient. By way of example, use is made in this case of so-called intraoral cameras, which contain a handpiece, the front end region of which is introduced into the mouth of a patient. In general, a light-entrance or viewing window for the camera optics is situated in this end region, from which window the image of the object to be examined is transmitted to a capture apparatus, e.g. a CCD chip. This conventional intraoral camera can furthermore be extended to form a system for transilluminating teeth, as is known, for example, from DE 10 2006 041 020 A1, filed by the applicant. In this case, the tooth to be examined is irradiated by visible light, with an optical image of the tooth illuminated by the examination radiation then being recorded and evaluated. Since carious sites on the tooth scatter the light differently than healthy tooth tissue, such sites can be identified when capturing the tooth with the aid of a camera.

Both cases are problematic in that the quality of the image obtained is only satisfactory if the viewing window in the front region of the handpiece allows an uninhibited entry of light. However, in the case of such intraoral cameras, the temperature differences between within and outside of the oral cavity of a patient often result in the problem that the window steams up after the camera is introduced into the oral cavity. A similar problem also occurs in other medical fields, in which optical recordings from the interior of a patient to be examined should be generated with the aid of a catheter for example.

Heating the window has already been proposed in order to avoid the problem of the window for the camera steaming up. Previously known solutions for this are based on thermal coupling between light sources in the interior and the window, and on the targeted heating of the camera in external repository apparatuses.

Thermal coupling between light sources in the interior and the window was enabled, for example, by the use of LEDs and the accompanying placement close to the camera window. It is well known that LEDs produce a not insignificant amount of waste heat, which can then be utilized for heating the window via the thermal radiation resulting therefrom. However, a disadvantage of this solution is that placing the illumination means at the distal end of the handpiece leads to an enlargement of the instrument, which is generally undesirable as a result of the spatially limited oral cavity. Furthermore, this solution provides no options for regulating the heating of the window at different ambient temperatures.

Heating the camera handpiece in an external repository is disadvantageous in that the handpiece—in order to maintain readiness at all times—should in principle be arranged in this repository. Furthermore, this solution is bound up with the requirement of an additional current supply.

SUMMARY OF THE INVENTION

The present invention is therefore based on the object of specifying a novel solution for avoiding the aforementioned problems. In particular, the option of heating the viewing window of a medical or dental diagnostic device, which has image capture means, should be made possible in a simple and effective fashion.

Accordingly, the invention provides a medical, in particular dental, diagnostic device with means for image capture and with a handpiece, which has a window situated in the beam path of the means for image capture, and means for heating the window, wherein the means for heating the window is a resistance heater.

The solution according to the invention is based on the idea of heating the camera window with the aid of a resistance heater.

According to the invention, a medical, in particular a dental, diagnostic device with means for image capture and with a handpiece, which has a window situated in the beam path of the means for image capture, is accordingly proposed, with provision furthermore being made for means for heating the window and the means for heating the window being formed by a resistance heater.

The solution according to the invention is distinguished by virtue of the fact that it allows shifting of the illumination bodies in the direction of the proximal end of the handpiece whilst implementing an independent window heater. This allows the head region of the handpiece to have a particularly compact design, which has clear advantages in view of handling of the device and carrying out of examinations. Furthermore, the solution according to the invention leads to very precise and reliable heating of the window, leading to additional advantages during operation.

As per an advantageous development of the invention, the resistance heater can have a circuit-board conductor arrangement, which is arranged e.g. directly on an optically transparent substrate that forms the window. However, the circuit-board conductor arrangement could also be arranged on a support element that is coupled to the substrate that forms the window. By way of example, this support element can be a conventional printed circuit board, a so-called molded interconnected device (MID) as a two-component plastics injection-molding part or an MID as a single-component plastics injection-molding part, which was produced using the laser direct structuring (LDS) method. Here, the support element can have additional further electronic components, for example resistors or temperature-measuring elements. If temperature-measuring elements are used, the means for heating the window preferably also comprise a control unit designed to regulate a current flowing through the circuit-board conductor arrangement. This can achieve reliable heating of the camera window within a desired temperature range.

As an alternative to this, there would also be the option of using a so-called positive temperature coefficient (PTC) element. This element, which is often also referred to as a posistor element, may then be selected in such a way that a self-regulating heater is achieved and, in particular, the required maximum temperature of the camera window is not exceeded in order to avoid thermal irritations and burns. Thus, additional temperature sensors for detecting the actual window temperature and optionally switching off the heater circuit can be dispensed with in this case. Finally, there would also be the option of using a resistance wire situated in the vicinity of the window, for heating the window.

The means for heating the window are preferably coated or integrated into insulating material in order to maintain the required leakage paths and clearance. This can eliminate endangering the patient whilst using the device.

The diagnostic device according to the invention can more particularly be an intraoral camera or a device that is a component of a system for transilluminating teeth. However, the concept of the window heater according to the invention can also be applied to other medical diagnostic devices, for example catheters, endoscopes or the like.

BRIEF DESCRIPTION OF THE DRAWINGS

In the following text, the invention should be explained in more detail on the basis of the attached drawing, in which.

DETAILED DESCRIPTION

Figure 1A:
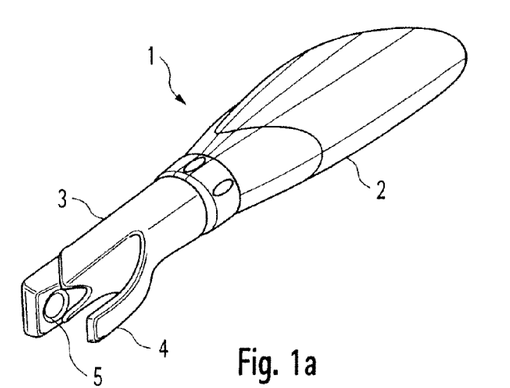
FIGS. 1a and 1b show views of the front region of a medical handpiece, which is a component of a system for transilluminating teeth.
Figure 1B:
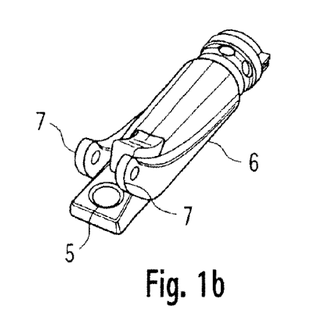

FIGS. 1a and 1b show, as a conceivable application example of the present invention, the front end region of a handpiece that is used in a system for transilluminating teeth. The handpiece, denoted by reference sign 1, has an elongate grip sleeve 2, with an attachment 3 being arranged at the front end thereof. This attachment 3 is used firstly to radiate light onto a tooth to be examined (not illustrated) and secondly to capture and evaluate the image, generated in the process, of the illuminated tooth.

The examination radiation usually has a wavelength in the range between approximately 550 nm and 790 nm, for example approximately 670 nm. The principle of this optical examination is based on the fact that the tissue of the tooth does not completely block the examination radiation but rather allows the radiation to pass through the tooth. In the process, the radiation is partly scattered, with carious regions in particular ensuring that the light is influenced in a characteristic fashion. If the tooth transilluminated thus is observed from different viewing directions, carious regions can be identified because these appear slightly darker.

In order to ease the handling of the device during the examination, the dimensions of the front end region in particular should be as small as possible. Accordingly, neither the light sources nor the actual means for image capture, e.g. a CCD chip, are arranged in the attachment 3 itself in the illustrated example (although it goes without saying that the application of the principle according to the invention would also be possible if the chip were to be arranged in the attachment 3), but these are rather situated in the rear part of the handpiece 1. In order to illuminate the tooth, the light emitted from the light sources arranged in the handpiece 1 is then coupled into the attachment 3 via optical waveguides and emitted from the attachment via a light-emergence element, which is arranged on a lower arm 4. A window 5, which is usually circular, is arranged opposite the light-emergence element and the image of the illuminated tooth is captured through it. The window 5 is coupled to the image capture means via optical elements, with use in this case predominately being made of mirrors, prisms, lenses and the like.

FIG. 1b shows a second form of an attachment 6, with the tooth to be examined in this case not being irradiated from the side opposite the window 5, but at an angle to it. To this end, the attachment has two lateral arms 7, at the end region of which the light-emergence ends of optical waveguides again are arranged, the optical waveguides being coupled to the internal light sources.

A high-quality image can only be obtained in both variants if the light ingress via the window 5 is unimpeded. A problem in this case in particular lies in the fact that the different temperatures within and outside of the oral cavity of a patient, and different values of the air humidity, can lead to the window 5 steaming up, which results in it not being possible, at least temporarily, to make optical recordings. In order to avoid this effect, provision is made for actively heating the window 5, with, according to the present invention, a resistance heater being used for this.

Figure 2:
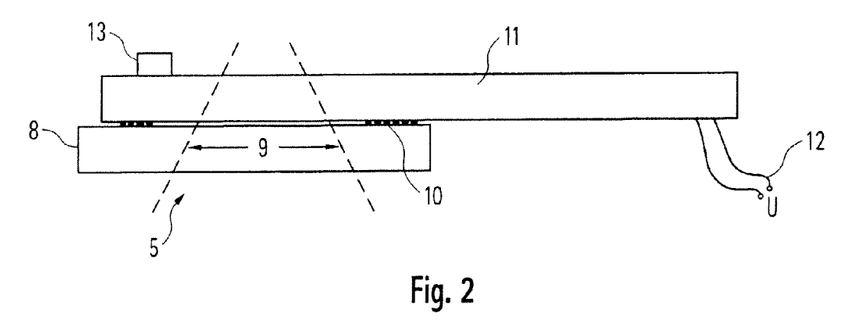
FIG. 2 schematically shows the embodiment of a first exemplary embodiment of a device according to the invention for heating the camera window.
Figure 3:
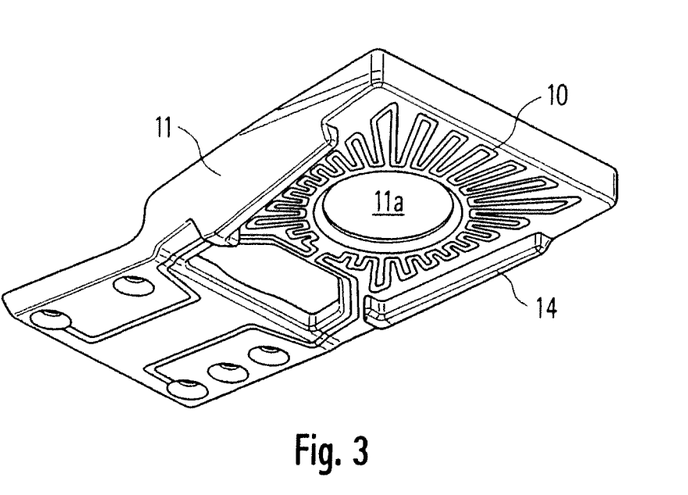
FIGS. 3 to 5 show further views for a more detailed embodiment of the heater as per the variant illustrated in FIG. 2.
Figure 4:
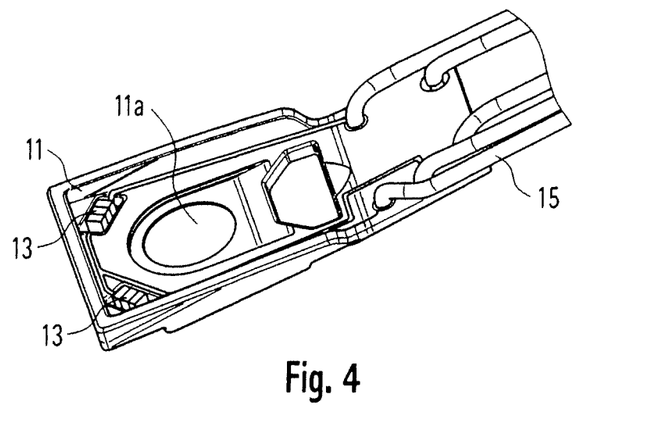
Figure 5:
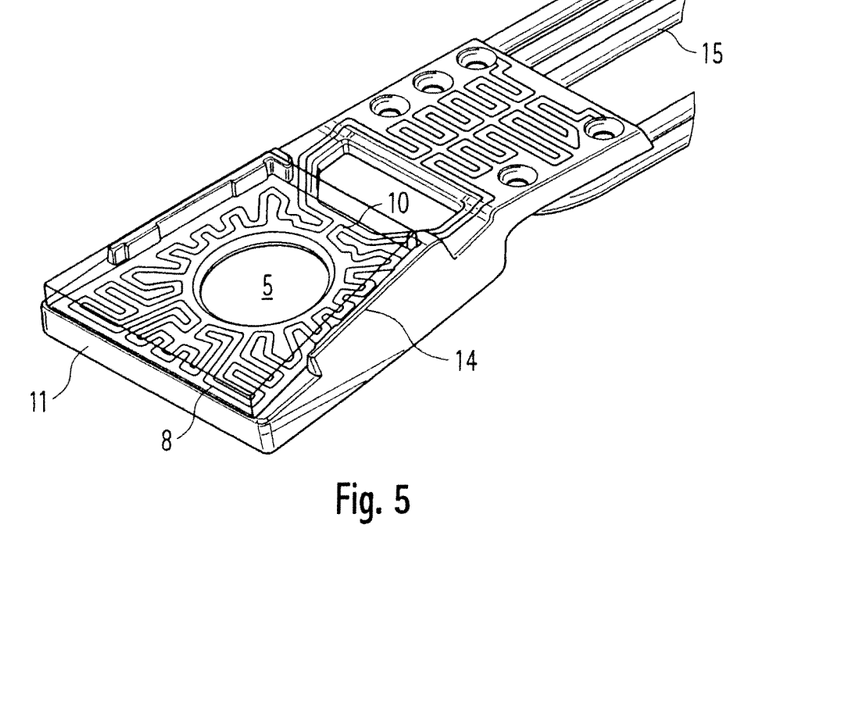

A first exemplary embodiment of the concept according to the invention is illustrated in FIGS. 2 to 5, with FIG. 2 schematically showing the embodiment of the window heater according to the invention and FIGS. 3 to 5 showing a specific embodiment.

The first variant of the solution according to the invention is based on the idea of directly heating the window 5 via a resistance heater. To this end, provision is made for an arrangement of circuit-board conductors 10 that are directly connected to the window substrate 8 and thermally coupled to it. By way of example, the window substrate 8 can consist of fused quartz, sapphire, plastics or another optically transparent material. The circuit-board conductors 2 can be applied directly onto the window substrate 8, but they are preferably arranged on the surface of a support element 11. This support element 11 can be a conventional printed circuit board or a so-called molded interconnected device (MID), which can be embodied as a two-component plastics injection-molding part or a single-component plastics injection-molding part, which was produced using the LDS method. It goes without saying that the alternative methods for producing a MID would also be feasible. In this context, reference is in particular made to hot foil stamping, in-mold film coating, film spray coating or similar methods.

The circuit-board conductors 10 are arranged in the vicinity of the window 5 in such a way that they are situated outside of the optical passage 9 for the camera optics and accordingly do not interrupt the image transmission to the image capture means. If a voltage is now applied to the circuit-board conductor arrangement 10 via a schematically illustrated power supply source 12, this leads to the generation of waste heat as a result of the resistance of the circuit-board conductors 10, which waste heat directly leads to the window 5 being heated as a result of the optimized arrangement of the circuit-board conductors 10. This can very effectively prevent the window 5 from steaming up.

The illustrated variant, in which the circuit-board conductors 10 are arranged on the support element 11, in this case allows the option of arranging additional electronic components, e.g. resistors or the like, on the support element 11 and connecting them to the circuit-board conductors 10. Here resistors are preferably once again arranged in the vicinity of the window 5 in order to obtain additional heating.

The temperature is monitored by one or more temperature-measuring elements 13, which are likewise arranged on the support element 11 in the vicinity of the window 5. It is possible to determine the temperature of the window 5 sufficiently accurately taking into account the necessarily resulting temperature difference between the side facing the window 5 and the side facing away from the window 5. This information is then processed by a control unit (not illustrated in any more detail), which accordingly actuates the power supply source 12 and as a result allows precise regulation of the window temperature.

In the case of an application of the window heater according to the invention in the medical field, it goes without saying that dangers to the patient should be eliminated, which is why the applicable standards in respect of clearance and leakage paths have to be met. This leads to plastics injection-molding methods being preferred when producing the support element 11 with the circuit-board conductors 10 because in this case suitable screening elements can be attached in the surroundings of the circuit-board conductors 10. These screening elements 14 illustrated in FIG. 5 allow the prescribed clearance and leakage paths to be obtained. In general, the sought-after safety of the patent can be ensured by a suitable coating of the circuit-board conductors 10, which coating can be produced in a relatively simple fashion when a plastics injection-molding method is used.

FIGS. 3 to 5 show the specific embodiment of a support element 11 embodied according to the invention, with equivalent elements being provided with the same reference signs.

The support element 11 here has a passage opening or an optical opening 11a, which allows the passage of light through the window 5 and the further routing to the image-capture means. It is furthermore possible to identify that several flexible leads 15 lead to the rear side of the support element 11, the circuit-board conductors 10 being fed with current via these flexible leads 15. The circuit-board conductors are preferably arranged meanderingly in the surroundings of the optical opening 11a so that the window substrate 8 can be heated over its entire surface and hence very effectively. The signals emitted by the temperature-measuring elements 13 are also transmitted to the control unit by the flexible leads 15.

The solution according to the invention is firstly distinguished by virtue of the fact that the window substrate 8 can be heated in a very fast and effective fashion. Furthermore, the means for heating the window 5 only require little space, and so they can be arranged directly in the vicinity of the window 5 (as illustrated), as a result of which the effectiveness of the heater is additionally increased.

Figure 6:
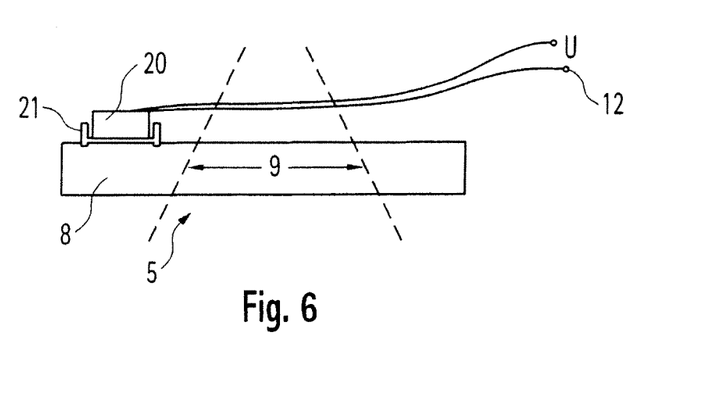
FIG. 6 schematically shows a second exemplary embodiment of a window heater according to the invention.
Figure 7:
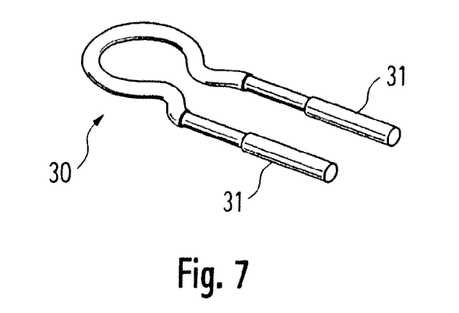
FIGS. 7 to 10 show a resistance wire utilized to heat the camera window.
Figure 8:
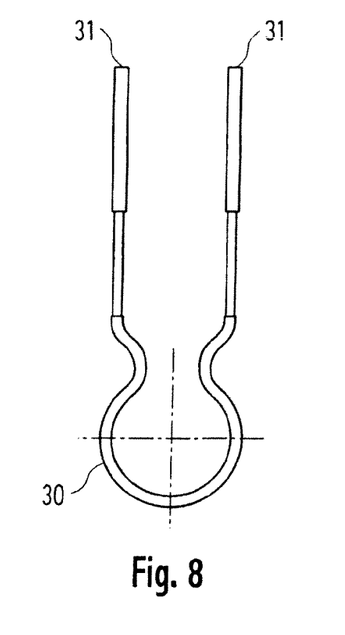
Figure 9:
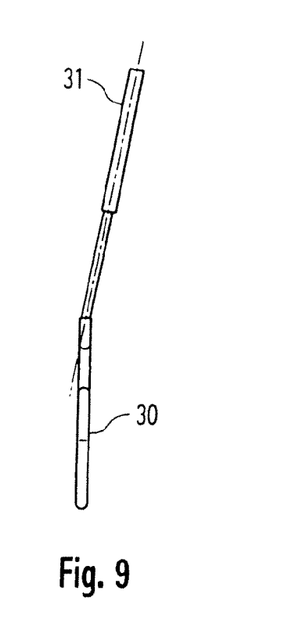
Figure 10:
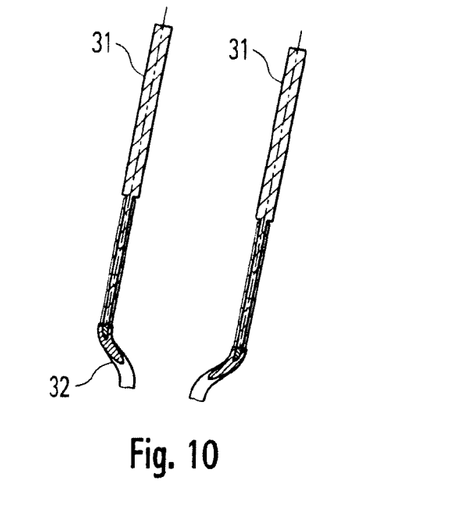

A further embodiment of the window heater according to the invention is illustrated schematically in FIG. 6. Here, the window substrate 8 is now heated with the aid of a so-called posistor element 20 or positive temperature coefficient (PTC) element. Feeding current to the PTC element 20 once again brings about heating, with the resistance characteristic of the posistor element 20 being selected so that the element 20 acts in a self-regulating fashion and accordingly the required maximum temperature of the window 5 is not exceeded in order to avoid thermal irritation and burns. Additional temperature sensors for recording the actual window temperature and switching off the heater circuit are not required in this case.

Depending on the embodiment of the window 5, the PTC element 20 can be applied directly or indirectly to the window substrate 8. Thermal coupling and electrical insulation can be brought about by adhesive bonding and/or pressing on.

In this second variant, the flexible leads 15 illustrated in FIGS. 4 and 5 can be connected directly to the PTC element 20, e.g. soldered on or connected via pin contacts, snap-in contacts or similar suitable flexible elements. Thermally conducting and electrically insulating materials, more particularly ceramics (e.g. $Al_3O_2$) or plastics with ceramic fillers, e.g. silicones with ceramic fillers for improving the thermal conductivity, can be used as insulation elements 21 for maintaining the required clearance and leakage paths. In order to optimize the thermal connection, thermally conducting materials are introduced here between the individual layers. Such elements can also be used to compensate for inexpedient shape or dimensional tolerances.

A further option for implementing a window heater according to the invention consists of using a resistance wire 30, as illustrated in FIGS. 7 to 10. Depending on the design of the window, the resistance wire 30 can be applied directly onto the window substrate or attached by means of one or more insulation elements. In this case, the resistance wire 30 can be directly soldered, crimped, or similarly attached to two current-feeding flexible leads 31. Special measures are also required in this case for maintaining the applicable standards in respect of clearance and leakage paths. The resistance wire must accordingly be coated by an electrical insulation 32, wherein a tube, a plastic or a ceramic part could be used for this purpose. The resistance wire 30, shaped in a loop and with or without insulation, can then be adhesively bonded or pressed onto the window substrate—not illustrated—by means of suitable elements.

Finally, a further option for heating the window would also consist of using so-called heat pipes, which ensure thermal coupling between heating source and window substrate.

Figure 11:
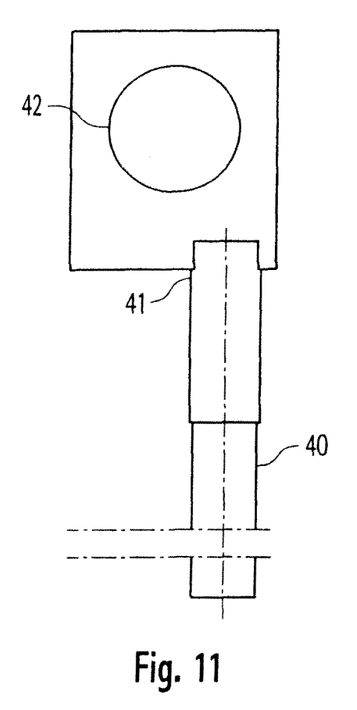
FIGS. 11 and 12 show a first variant for heating the camera window by means of a so-called heat pipe.
Figure 12:
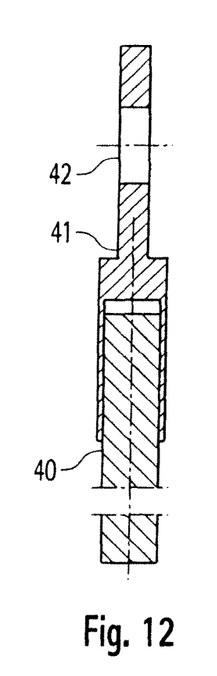

In the example illustrated in FIGS. 11 and 12, a heat pipe 40, known per se, has been provided with an additional element in the form of a heat exchanger sheet 41 with a hole 42 that can be situated in the center of the window to be heated. It serves for heating the window as homogeneously as possible. The additional element 41 is in this case soldered onto the heat pipe or connected to it by any other means. An advantage of this variant consists of being able to shift the actual heat source, i.e. the resistance heater, and hence the critical regions in respect of clearance and leakage paths into regions of the handpiece that are less critical in respect of the available space. The actual heating of the heat pipe then takes place in this region.

Figure 13:
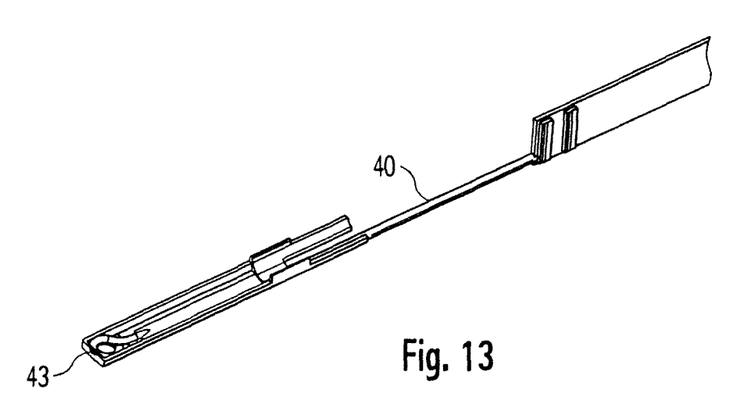
FIG. 13 shows a second variant for heating the camera window by means of a heat pipe.

FIG. 13 finally shows a second embodiment of thermal coupling by means of a heat pipe 40, which is now once again designed in a loop shape fashion in the front region 43, which is arranged on the window substrate.

In effect, the solution according to the invention provides an option for heating the window in an intraoral camera in a simple and effective fashion. The compact design of the heater according to the invention furthermore ensures a small installation size of the head region of the camera, which leads to improved handling of the device.

The invention claimed is:

1. A dental diagnostic device, comprising:
a handpiece having a front end, a rear end disposed opposite the front end, a light emergence element arranged proximate to the front end, a window arranged proximate to the front end, and a support element coupled to the window, the light emergence element and the window being arranged to receive a tooth situated between the light emergence element and the window, the window being further arranged to receive light from the tooth, the support element comprising a printed circuit board having an opening arranged adjacent the window to receive the light after the light has passed through the window; and
the printed circuit board comprising a resistance heater printed on the printed circuit board and thermally coupled to the window to actively heat the window, the resistance heater including a plurality of conductors connected to one another to form a zig-zag pattern.

2. The dental diagnostic device of claim 1, wherein the support element is coupled to an optically transparent substrate that forms the window.

3. The dental diagnostic device of claim 2, comprising further electronic components arranged on the support element.

4. The dental diagnostic device of claim 1, further comprising temperature-measuring elements and a control unit configured to regulate a current flowing through the circuit-board conductor arrangement.

5. The dental diagnostic device of claim 1, wherein the resistance heater is coated.

6. The dental diagnostic device of claim 1, comprising an intraoral camera.

7. The dental diagnostic device of claim 1, wherein the device is a component of a system for transilluminating teeth.

8. The dental diagnostic device of claim 1, wherein the support element has a first end coupled to and positioned immediately adjacent the window and a second end disposed opposite the first end at a position more proximate to the rear end of the handpiece than the first end.

9. A dental diagnostic device, comprising:
a handpiece having a front end, a rear end disposed opposite the front end, a light emergence element arranged proximate to the front end, a window arranged proximate to the front end, and a support element coupled to the window, the light emergence element being arranged to direct first light into a side portion of the tooth to produce second light from a top portion of the tooth, and the window being arranged to receive the second light from the top portion of the tooth while the light emergence element directs the first light into the side portion of the tooth, the support element comprising a printed circuit board having an opening arranged adjacent the window to receive the second light after the second light has passed through the window; and
the printed circuit board comprising a resistance heater printed on the printed circuit board and thermally coupled to the window to actively heat the window, the resistance heater including a plurality of conductors connected to one another to form a zig-zag pattern.

10. A dental diagnostic device, comprising:
a handpiece having an elongate grip sleeve and an attachment arranged at a front end of the elongate grip sleeve, the attachment including a light emergence element, a window, and a support element coupled to the window, the light emergence element and the window being arranged to receive a tooth situated between the light emergence element and the window, the window being further arranged to receive light from the tooth, the support element comprising a printed circuit board having an opening arranged adjacent the window to receive the light after the light has passed through the window; and
the printed circuit board comprising a resistance heater printed on the printed circuit board and thermally coupled to the window to actively heat the window, the resistance heater including a plurality of conductors connected to one another to form a zig-zag pattern.

11. The dental diagnostic device of claim 10, further comprising a light source for the light emergence element arranged within the elongate grip sleeve.

12. The dental diagnostic device of claim 11, wherein the light source is arranged in a rear portion of the elongate grip sleeve.

13. The dental diagnostic device of claim 10, wherein the attachment includes a first outwardly extending arm and a second outwardly extending arm, the first outwardly extending arm comprising the light emergence element, and the second outwardly extending arm comprising the window.

* * * * *